United States Patent [19]

Michelson

[11] Patent Number: 4,628,933
[45] Date of Patent: Dec. 16, 1986

[54] METHOD AND APPARATUS FOR VISUAL PROSTHESIS

[76] Inventor: Robin P. Michelson, 886 Edgewood Rd., Redwood City, Calif. 94062

[21] Appl. No.: 758,609

[22] Filed: Jul. 23, 1985

[51] Int. Cl.$^4$ .......................... A61N 1/36; A61F 1/16
[52] U.S. Cl. ................................ 128/419 R; 128/784; 623/4
[58] Field of Search ............ 128/419 R, 745, 783–784; 623/4, 11, 24

[56] References Cited

U.S. PATENT DOCUMENTS

| 2,760,483 | 8/1956 | Tassicker | 623/4 |
| 4,551,149 | 11/1985 | Sciarra | 623/4 |

FOREIGN PATENT DOCUMENTS

| 1943956 | 5/1971 | Fed. Rep. of Germany | 128/419 R |
| 2016276 | 9/1979 | United Kingdom | 623/4 |

OTHER PUBLICATIONS

Brueschke et al., "Electromagnetic Power Transfer System" *TransAm Soc Artif Intern Organs*, vol. 27, 1981, pp. 84–88.

Sherman et al., "Energy Transmission Across Intact Skin for Powering Artificial Internal Organs," TransAm Soc Artif Intern Organs, vol. 27, 1981, pp. 137–141.

Potts, A. M. et al., "The Electrically Evoked Response of the Visual System," *Invest. Ophy.* (1968) 7:269–278.

*Primary Examiner*—William E. Kamm
*Assistant Examiner*—Mitchell J. Shein
*Attorney, Agent, or Firm*—Townsend and Townsend

[57] ABSTRACT

A visual prosthesis for blindness due to retinal malfunction includes a compact device having a close-packed array of photosensitive devices on one surface thereof. A plurality of electrodes extend from the opposed surface of the device and are connected to the outputs of the photosensitive devices. The device is adapted to be inserted in the posterior chamber of the eye, generally disposed at the focal plane of the optical pathway and impinging on the retina. Anchoring means secure the device with the electrodes operatively connected to the neuron array at the surface of the retina to stimulate the neurons in a pattern corresponding to the illumination pattern of the photosensitive array. The device is powered by externally induced electromagnetic or radio frequency energy, and is encased in a biologically inert housing. An amplifier array may be interposed between the sensing elements and the electrodes to amplify, shape, and time-process the visual signals.

20 Claims, 7 Drawing Figures

U.S. Patent   Dec. 16, 1986   Sheet 1 of 2   4,628,933
FIG._1A.
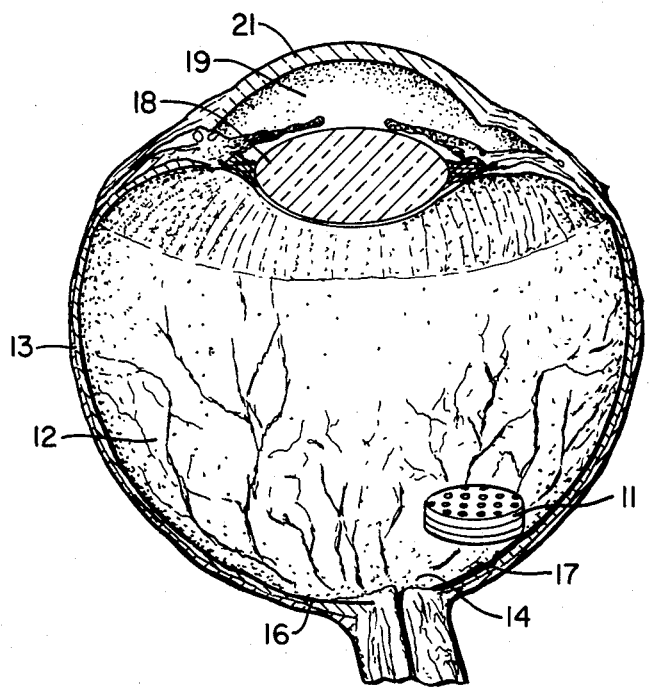
FIG._1B.
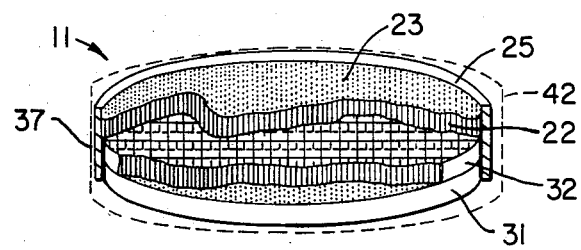
FIG._2.
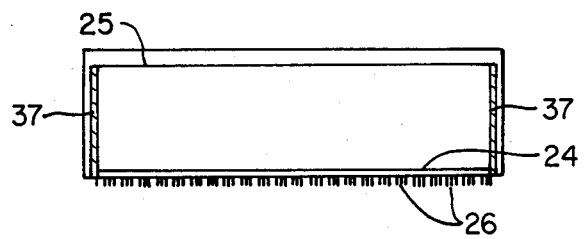
FIG._3.

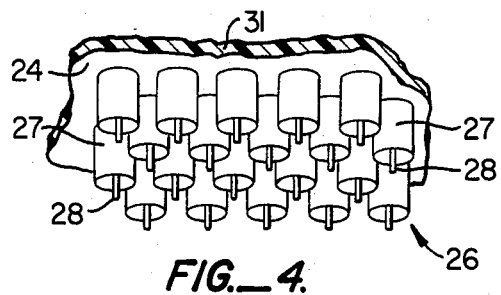
FIG._4.
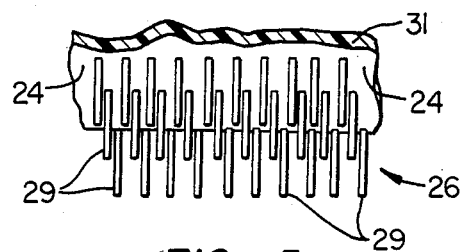
FIG._5.
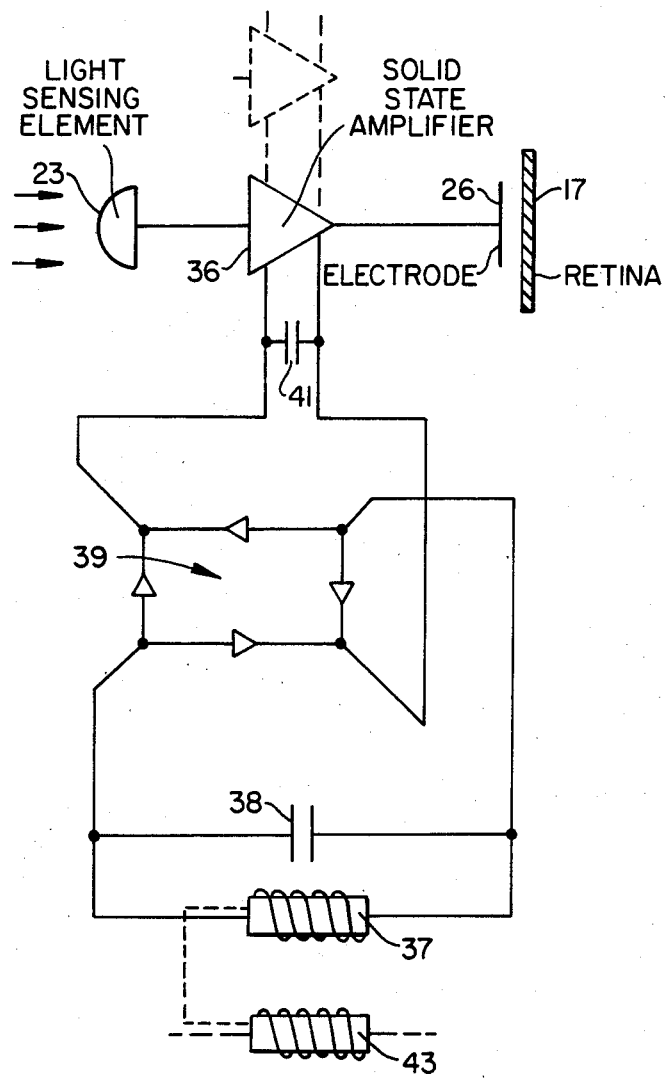
FIG._6.

METHOD AND APPARATUS FOR VISUAL PROSTHESIS

BACKGROUND OF THE INVENTION

1. Field of the Invention

The present invention is generally directed to a method and apparatus for inducing visual preception in persons suffering from blindness caused by retinal disease, pathology, or malfunction. Many causes of blindness, especially those involving occlusions or opacity in the optical pathway through the eye, have yielded to modern medical treatments, and vision can be restored to a great extent in a large number of cases. Indeed, the removal of cataract-occluded lenses is now a mere outpatient surgical procedure, and the substitution of plastic lens implants yields excellent results. Likewise, relief from secondary cataracts in the posterior capsule of the lens may be corrected using optical laser eye surgery in a noninvasive procedure requiring only minutes to complete.

Some diseases of the eye, however, cause blindness by attacking the light-sensing retina, causing blindness while the remainder of the optical pathway remains perfectly clear and functional. For example, the genetically transmitted disease retinitis pigmentosa gradually causes destruction of the rod and cone cells in the retina, resulting in eventual total blindness. It is interesting that this disease does not adversely affect the optic nerve, nor the neurons in the retina. It is known that other diseases affecting the retina likewise leave many viable neurons in the retina.

Recent research and development in the field of sensory deafness has shown that such deafness can be overcome, and intelligible hearing can be induced by direct electrical stimulation of the auditory nerve endings distributed along the basilar membrane in the cochlea of the inner ear. By properly filtering, processing and channeling spectral portions of the electrical audio signal analog of ambient sound to appropriate portions of the basilar membrane, significant word recognition can be achieved by individuals who were formerly completely deaf. These successful developments suggest that direct electrical stimulation of visual neurons should be able to provide at least some degree of visual cueing to persons suffering from sensory blindness.

2. Description of the Relevant Literature

Michelson, R. P., "Electrical Stimulation of the Cochlea," *Gerald English's Otolaryngology*, Harper and Row Publishers, Inc., 1980.

Potts, A. M., et al., "The Electrically Evoked Response of the Visual System," *Invest. Ophy.* (1968) 7:269–278.

SUMMARY OF THE INVENTION

The present invention generally comprises a method and apparatus for inducing visual response in individuals suffering from sensory blindness; i.e., blindness caused by lack of proper functioning of the light-sensing rod and cone cells in the retina.

The apparatus includes a visual prosthesis, comprising a compact device having a close-packed array of photosensitive devices on one surface thereof. The light-sensing devices may comprise light-sensing diodes, a charge-coupled device sensing array, or light-sensing dipoles. A plurality of electrodes extend from the opposed surface of the device and are connected to the outputs of the photosensitive devices. The device is adapted to be inserted surgically in the posterior chamber of the eye, generally disposed at the focal plane of the optical pathway and impinging on the retina. Anchoring means secure the device with the electrodes operatively connected to the neuron array at the surface of the retina to stimulate the neurons in a pattern corresponding to the illumination pattern of the photosensitive array.

The prosthesis is housed in a case formed of a biologically inert substance which is also transparent, such as glass, inert polymer, or the like. The electrodes may be fabricated as a "bed of nails" array extending from a ground plane, or alternatively, as individual coaxial elements which control the shape and extent of the electrical field at the distal end of each electrode. In either case, the electrodes may be coated with an impedance controlling substance, such as iridium oxide or barium titanate, to prevent the accumulation of toxic compounds liberated at the tissue-metal interface due to electrochemical action.

The device is powered by externally induced electromagnetic or radio frequency energy, either directly or through a rechargeable battery. A tuned inductor is secured about the device, or formed on one surface of the device, to receive operating energy from a source external to the eye. An amplifier array may be interposed between the sensing elements and the electrodes to amplify, shape, and time-process the visual signals. For example, the optimum stimulating signal may be a charge-balanced AC waveform, with no net charge remaining to cause electrolysis and liberate toxic compounds. Also, the signal should be provided to the neurons at a frequency which closely matches the firing rate of the neurons during activation.

IN THE DRAWINGS

FIGS. 1A and B are a cross-sectional elevation of the human eye, showing the prosthesis of the present invention implanted therein;

FIG. 2 is a partially cut-away perspective view of one embodiment of the prosthesis of the present invention;

FIG. 3 is a side elevation of the prosthesis of the present invention;

FIG. 4 is an enlarged perspective view of one embodiment of the electrode array of the present invention;

FIG. 5 is an enlarged perspective view of another embodiment of the electrode array of the present invention; and FIG. 6 is a simplified schematic representation of the circuitry of the prosthesis of the present invention.

DETAILED DESCRIPTION OF THE PREFERRED EMBODIMENT

The present invention generally comprises an apparatus and method for inducing visual perception in persons suffering from blindness due to malfunction or nonfunction of the light-sensing rod and cone cells in the retina of the eye, or like pathology which does not adversely affect the optical pathway of the eye nor the neural response of the retina.

With regard to FIG. 1B, the apparatus of the invention includes an ocular prosthesis 11 adapted to be implanted by surgical techniques in the posterior chamber 12 of an eye 13. The prosthesis 11 is secured directly adjacent to the retina 17 and impinging thereon, and is generally disposed in the vicinity of the macula 14. The prosthesis may be located between the optical disk and the macula lutea 16, the prime focus of the optical pathway consisting of the lens 18, the anterior chamber 19, and the cornea 21. This portion of the retina is densely packed with first order visual neurons emanating from the optic nerve.

With regard to FIG. 2, the prosthesis 11 is configured generally as a flat disk having a diameter of approximately one-half centimeter, and a height substantially less than the diameter. The disk includes an upper layer 22 having a large plurality of light-sensing devices 23 disposed therein in a regular array at the upper surface 25 of the prosthesis. The light-sensing devices may comprise approximately 500–1000 light-sensitive diodes, or light-sensitive dipole devices, or charge-coupled devices (CCD). Recent advances in CCD technology have placed over 9000 pixels per square millimeter on an integrated circuit substrate. This device packing density approaches the density of the naturally-occurring light sensitive rod and cone cells in the retina, and can provide more detailed resolution than photodiodes, which are relatively larger devices. The signals from pixels of charge-coupled devices are typically read out sequentially, rather than in parallel. In any case the layer 22 is preferably an integrated circuit substrate, with the light-sensing devices formed integrally therein to maximize device density and resolution.

The prosthesis 11 includes a layer 31 with a surface 24 opposite to the surface 25 and provided with a plurality of electrodes 26 extending therefrom in a regular array. The electrodes 26 are connected to the outputs of the photosensitive devices 23, either directly or indirectly, and are adapted to communicate with the first order visual neurons which line the surface of the retina 17. Thus, the electrical signals generated by the photosensitive devices 23 stimulate the visual neurons to produce visual perception. The two-dimensional pattern of activation of the devices 23, located at the optical focal plane, is applied to the neurons in a corresponding two-dimensional pattern, so that perception of light and dark shades and objects, at least in gross form, may be obtained.

With regard to FIG. 4, one embodiment of the electrodes 26 comprises coaxial elements having a plurality of inner conductors 28, each surrounded by a concentric, grounded outer coaxial shield 27. As is known in the prior art, the outer shielding member 27 confines the electric field emanating from the electrode so that the electrical stimulus will not spread to adjacent neurons and cause spurious neuron activation. Also, the extension of the electrode with respect to the distal end of the respective coaxial shield may be trimmed selectively to further shape and confine the stimulating electrical field to the neuron directly adjacent to the electrode.

Another embodiment of the electrodes 26, depicted in FIG. 5, includes an array of short, rod-like conductors 29 extending from the lower surface 24 of the prosthesis. The conductors 29 are disposed in a regular array to form a "bed of nails" configuration which contacts the retinal neurons. In this embodiment the lower surface 24 is the outer surface of a ground plane 31 which also controls and limits the electrical fields emanating from the conductors 29, though not to the extent of the coaxial embodiment.

In either of the embodiments of FIGS. 4 and 5, it is necessary to overcome any electrochemical or electrolysis effects caused by the potential difference between the charged electrode (28 or 29) and ground (27 or 24). At the tissue-metal interface there is a significant intrinsic capacitance. If a net charge remains between the two conductors, ions such as chloride may migrate to the oppositely-charged conductor, causing polarization of the conductors and degradation of the neural stimulation. Moreover, such polarization can result in the liberation of metal ions at the tissue-metal interface. Over the course of time the metal ions may accumulate to toxic levels, causing severe pathology.

One method for overcoming this problem is to connect a large resistor between the ground conductor and the signal conductor. This expedient will bleed off any residual charge and alleviate the problem. Another solution to the problem is to coat the electrodes (signal and ground) with a substance such as barium titanate or iridium. Such substances are conductive, yet are stable in impedance and tend not to become polarized.

The ideal visual neuron stimulating signal should take into account the following physiological factors: (1) the threshold for exciting optic neurons in terms of voltage, current, and optimal waveform, (2) the minimum stimulus time required to produce a visual pixel, (3) the dynamic range of the stimulated neuron, (4) the amount of movement of the exciting electrical field that the visual system can detect, (5) electrode impedance, and (6) the minimum size of the stimulating electrical field.

Means for adapting to the latter factors, electrode impedance and the size of the electrical field, have been described in the foregoing. The threshold, waveform, timing, and movement factors may require that the signals from the photosensitive elements 23 be amplified, shaped, and processed to optimize the neural stimulation to produce the best induced visual perception. For example, a charge-balanced square wave signal generates no residual electrical charge at the tissue-metal interface of the electrodes, and greatly aids in alleviating the electrode polarization problem noted above.

To adapt the signals from the devices 23 to the input characteristics of the neurons, the prosthesis of the present invention also includes a layer 32 interposed between the photodetector array and the electrode array. The layer 32 preferably comprises an integrated circuit, including electronic devices for amplifying, shaping, triggering and timing the inputs from the photodetectors to form the optimal neural excitation signals. By way of example, the human neural transmission channel has an upper frequency bandwidth limit between 1 and 2 kHz. Clearly, it is desirable to limit the frequency of the stimulation signal to within this bandwidth, and perhaps to a small portion of this bandwidth.

A simplified representation of the circuitry embodied in the integrated circuit layer 32 is depicted in FIG. 6. Each light-sensing element 23 is connected as an input to a transistor amplifier or an operational amplifier, if small enough, 36. The output of each amplifier 36 is conducted to a respective one of the electrodes 26 which impinge directly on the retina 17. Ancillary devices such as capacitors and resistors may be connected to the amplifiers 36, using techniques known in the prior art, to tune the responses thereof to the frequency response bandwidth of the retinal neurons, to shape the output waveform in a charge-balanced square wave format, and to trim the voltage and current outputs to acceptable levels for the neurons. It should be noted that the first order retinal neurons lie on the inner surface of the retina, while the light-sensing rod and cone cells are embedded within the retina. Thus, the electrode 26 makes direct contact with the visual neurons to apply direct electrical stimulation thereto.

The electronic circuitry requires electrical power for operation, and direct connection to a power source is not readily available within the eyeball. One means of providing power to the prosthesis 11 is through electromagnetic or radio frequency induction. An inductor coil 37 may be wound about the periphery of the assembled layers 22, 32, and 31, or may be formed by photolithographic circuit techniques on one of the surfaces of one of the layers. In either case the inductor 37 is connected in parallel with an internal capacitor 38 to form a tuned LC tank circuit therewith. An electromagnetic or RF field operating at the resonant frequency of the tank circuit induces an AC voltage in the inductor 37. The tuned circuit is connected to a full wave bridge rectifier 39, and the DC output of the rectifier is connected to each of the amplifiers 36. A capacitor 41 connected between the outputs of the rectifier removes any AC ripple in the output. The transmitting field which provides the power is generated by a similarly tuned resonator coil 43 disposed adjacent to the eye. One advantageous placement of the transmitter is about an eyeglass frame lens opening, so that the axis of the transmitting coil is oriented directly toward and in alignment with the axis of the coil 37.

In the embodiment which employs CCD image sensors or others, it is necessary to scan the CCD pixels serially, amplify and shape the signal, and scan the electrodes 26 to deliver the signal to the appropriate output conductor in the raster pattern. The timing of this process may be aided by the constant frequency of the inductive power signal, which can be obtained from the tuned receiving circuit. In some embodiments, it may be desirable to raster scan to prevent overlap of exciting fields.

It should be noted that the entire prosthesis 11, with the exception of the electrodes 26, is encased in a biologically inert, light transmissive housing 42. The materials for the housing may comprise a low temperature glass, an optical grade polymer, or the like. The presence and pressure of the surrounding vitreous humour may be sufficient to maintain the placement of the prosthesis 11 against the retina, in the same manner that it maintains the retina in place against the choroid structure of the eye. Anchoring means such as nonconductive posts (not shown) may also be required, extending from the housing 42 through the retina to the underlying sclera tissue to secure the prosthesis in place.

I claim:

1. A visual prosthesis for implantion in the eye in the optical pathway thereof, including a plurality of photosensitive elements disposed in an array at one surface of said prosthesis and oriented to receive light entering the eyeball, a plurality of electrode means extending from a second surface of the prosthesis and for contacting the visual neurons at the surface of the retina of the eyeball, and means for transferring the output signals from said plurality of photosensitive elements to said plurality of electrode means in a pattern corresponding to the illumination pattern of said photosensitive array.

2. The visual prosthesis of claim 1, wherein said first and second surfaces are disposed on opposite sides of the prosthesis.

3. The visual prosthesis of claim 1, wherein said plurality of electrode means includes an array of rod-like conductors extending from said second surface, and said second surface comprises a ground plane.

4. The visual prosthesis of claim 1, wherein said plurality of electrode means includes a plurality of coaxial conductors, each having a signal conducting electrode surrounded by a shielding, coaxially extending electrode.

5. The visual prosthesis of claim 1, further including a housing extending continuously about all surfaces of the prosthesis, said electrode means extending outwardly through said housing.

6. The visual prosthesis of claim 5, wherein said housing is formed of an optically transparent, biologically inert material.

7. The visual prosthesis of claim 1, wherein said electrode means are coated with a conductive material which provides a constant impedance at the interface of said electrode means and the retinal surface.

8. The visual prosthesis of claim 7, wherein said conductive material comprises iridium oxide.

9. The visual prosthesis of claim 7, wherein said conductive material comprises barium titanate.

10. The visual prosthesis of claim 1, wherein said means for transferring said output signals includes amplifier array means disposed between said first and second surfaces.

11. The visual prosthesis of claim 10, wherein said amplifier array means includes a plurality of amplifiers, each connected between one of said photosensitive elements and one of said electrode means, for amplifying, shaping, and processing the output signal of the respective photosensitive element.

12. The visual prosthesis of claim 11, wherein each of said amplifiers is tuned to the nominal response bandwidth of the first order retinal neurons.

13. The visual prosthesis of claim 10, wherein said amplifier array means includes integrated circuit means for sequentially and serially scanning the output signals of said photosensitive elements, amplifying and processing said output signals, and sequentially and serially scanning said electrode means to electrically energize said plurality of electrode means in a pattern corresponding to the illumination pattern of said photosensitive elements.

14. The visual prosthesis of claim 1, further including means for transmitting electrical operating power from the exterior of the eyeball to the prosthesis, and further including means for receiving said electrical operating power.

15. The visual prosthesis of claim 14, wherein said means for receiving electrical power includes a tuned electromagnetic receiver in the prosthesis, and the means for transmitting includes an external electromagnetic transmitter tuned to said receiver.

16. The visual prosthesis of claim 15, wherein said receiver includes a resonant inductor tuned to a predetermined frequency.

17. The visual prosthesis of claim 15, further including rectifier means connected to said tuned receiver for converting the received alternating current signal to direct current operating power.

18. A method for inducing visual perception in the eye, comprising the steps of:

forming an array of photosensitive devices;

forming an array of biologically compatible electrodes;

connecting said arrays together, each photosensitive device having an output connected to one of the electrodes; and implanting said connected arrays in the posterior chamber of the eye, with said photosensitive devices disposed to intercept light entering the eye and with the electrodes impinging on the first order neurons at the surface of the retina to activate the neurons electrically in a pattern corresponding to the illumination pattern of the array of photosensitive devices.

19. The method of claim 18, further including the step of connecting the arrays by providing a further array of amplifiers connected therebetween, each amplifier of the array connected between one of the photosensitive devices and one of the electrodes to amplify and process the device output signal.

20. The method of claim 19, further including the step of transmitting electrical operating power to the implanted, connected arrays by transmitting an AC electromagnetic field from the exterior of the eye to an antenna connected to the arrays.

* * * * *